United States Patent [19]

Lee et al.

[11] Patent Number: 5,756,146

[45] Date of Patent: May 26, 1998

[54] INSPECTING COPPER OR MOLYBDENUM LINES ON A SUBSTRATE

[75] Inventors: Kang-Wook Lee, Yorktown Heights; Alfred Viehbeck, Fishkill, both of N.Y.

[73] Assignee: International Business Machines Corporation, Armonk, N.Y.

[21] Appl. No.: 815,826

[22] Filed: Mar. 12, 1997

[51] Int. Cl.$^6$ ............................................. H05H 1/00

[52] U.S. Cl. ...................... 427/10; 427/123; 427/125; 427/155; 427/256; 427/322; 427/352; 427/383.1; 427/404; 427/537; 427/555; 427/576

[58] Field of Search .................... 427/10, 123, 125, 427/155, 256, 322, 352, 383.1, 404, 537, 555, 576

[56] References Cited

PUBLICATIONS

Lee et al, Low–Cost and High–Temperature Stable Adhesion Promoter for Polymer–to–Copper Interface: Organic Compounds Containing Triazole or Imidazole Functionality, IBM Technical Disclosure Bulletin 37 (5): 221 (1994). (No month avail.).

Orbot Wafer Inspection System brochure (undated).

Viehbeck et al, Redox Seeding and Electroless Metallization of Polyimides, ACS Symposium Series 440, Metallization of Polymers: 394–414 (1990) (No month avail.).

*Primary Examiner*—Bernard Pianalto
*Attorney, Agent, or Firm*—Pollock, Vande Sande & Priddy

[57] ABSTRACT

Copper lines or molybdenum lines on a substrate are inspected for defects by coating a metallized substrate with an inspection layer followed by imaging the substrate, and removing the inspection layer after the imaging. The inspection layer can be a light reflecting metal or a combination of a light reflecting metal and light-absorbing organic compound.

31 Claims, No Drawings

INSPECTING COPPER OR MOLYBDENUM LINES ON A SUBSTRATE

DESCRIPTION

1. Technical Field

The present invention is concerned with inspecting copper and molybdenum lines on a substrate for defects in the copper and molybdenum lines. The process of the present invention is especially advantageous for thin film packaging processing, and more particularly in fabricating multichip modules.

According to the present invention, a copper and molybdenum metallized substrate is selectively coated with an inspection layer. The process further involves imaging the substrate and removing the inspection layer after the imaging. The preferred inspection layers are light reflecting metals.

2. Background of the Invention

The demand for multichip modules (MCM) is ever increasing so as to handle the greater memory and complexity of recent computing systems. Among the various MCM technologies, MCM-D (thin-film dielectric) is currently used primarily in mainframes and mid-range computing systems. The multilevel thin film process is a key to the success of MCM-D packages.

Polyimides and copper are typically used as dielectric and conducting layers, respectively. Polyimides derived from polyamic ester such as mPaete™ instead of polyamic acid have been employed in the current packaging process. mPaete is a polyimide based on pyromellitic dianhydride (PMDA) and oxydianiline (ODA, also named 4,4'-diaminodiphenyl ether). Electroless plated CoP is used to promote adhesion of polyimide on copper. However, the process employing CoP plating has two major disadvantages. The first one is that the plating process impregnates metal ions such as K, Co, and Cu into the mPaete dielectric layers due to reduction of PMDA-ODA by the CoP plating solutions. The second one is that the CoP layer in vias requires removal by a heavy ion beam process, and then the subsequently formed conductive haze layer (graphite-like material) requires removal by a heavy plasma ashing process. These processes are relatively expensive and time consuming.

In order to overcome these problems, new adhesion promoters to replace CoP have been investigated. For instance, AP420™ from Toray gave 20 g/mm peel strength while adenine or 8-azaadenine gave around 35–50 g/mm peel strengths. For instance, see Lee et al., Low-Cost and High-Temperature Stable Adhesion Promoter for Polymer-to-Copper Interface: Organic Compounds Containing Triazole or Imidazole Functionality, IBM Technical Disclosure Bulletin, Volume 37, No. 5, p. 221, May 1994. However, these techniques also suffer from certain disadvantages. In particular, the substrates with these new adhesion promoters and processes could not be inspected to check the status of all the copper lines and vias. The major problem of the inspection comes from the thin polyimide layer, which is transparent. Therefore, the metals in the top layer could not be distinguished from the bottom layer.

SUMMARY OF INVENTION

The present invention provides a process for inspecting copper and molybdenum lines on a substrate which overcomes problems in the prior art discussed above. In fact, the inspecting can be carried out with the tools and equipment that are currently used in manufacturing.

In particular, the present invention relates to a method for inspecting copper lines and molybdenum lines on a substrate for defects in the lines which comprises selectively metallizing a substrate with a pattern of copper lines or molybdenum lines.

The inspection layer is located either on all of the copper lines or molybdenum lines or over the entire non-metallized portions of the substrate. The substrate is then imaged to inspect it for defects in the copper lines or molybdenum lines. After imaging, the inspection layer is removed.

The inspection layer can be a light reflecting metal. The effectiveness of the inspection layer can be enhanced by introducing a light absorbing organic compound at certain regions of the inspection layer. In the case of the light reflecting metal, the coating is on the copper or molybdenum lines (i.e., the top or exposed copper or molybdenum lines). In the case of the light absorbing organic compound, the coating is on the substrate or on the buried copper or molybdenum lines. Advantages of also including the light absorbing compound include enhancing the contrast between light reflecting metal and the substrate, and in the case where the light absorbing layer is placed between top and bottom layers of copper or molybdenum, it prevents reflection of metal below the top layer.

BEST AND VARIOUS MODES FOR CARRYING OUT INVENTION

The process of the present invention is applicable to inspecting a wide variety of dielectric (non-conductor) substrates having copper or molybdenum lines thereon. The copper lines include not only copper per se, but also alloys of copper and especially those containing at least about 90 atomic % of copper. Likewise, the molybdenum lines include not only molybdenum, but also alloys of molybdenum, and especially those containing at least about 90 atomic % of molybdenum, such as molybdenum-tantalum alloys and molybdenum-titanium alloys. Dielectric substrates described including thermoplastic and thermosetting resins, may be employed in the present invention.

Typical thermosetting polymeric materials include epoxy, phenolic based materials, and polyimides. The dielectric materials may be molded articles of the polymers containing fillers and/or reinforcing agents such as glass filled epoxy or phenolic based materials. Examples of some phenolic type materials include copolymers of phenol, resorcinol, and cresol. Examples of some suitable thermoplastic polymeric materials include polyolefins such as polypropylene, polysulfones, polyethylene terephthalate, polycarbonates, nitrile rubbers, ABS polymers and polyimides.

The terms "substrate" and "surface," are employed herein, includes surfaces inside through holes or vias as well as major surface of a substrate.

Preferred polymeric materials subjected to the process of the present invention are the polyimides. The polyimides include unmodified polyimides such as polyester imides, polyamide-imide-esters, polyamide-imides, polysiloxane-imides, as well as other mixed polyimides. Such are well-known in the prior art and need not be described in any great detail. The polyimides are preferred in view of their continually expanding use in providing electronic devices and packaging and in view of their widespread availability.

Generally, the polyimides include the following recurring unit:

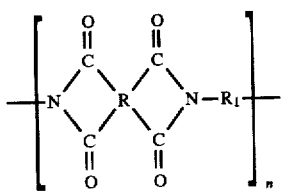

where n is an integer representing the number of repeating units to provide a molecular weight usually about 10,000 to about 100,000. R is at least one tetravalent organic radical selected from the group consisting of:

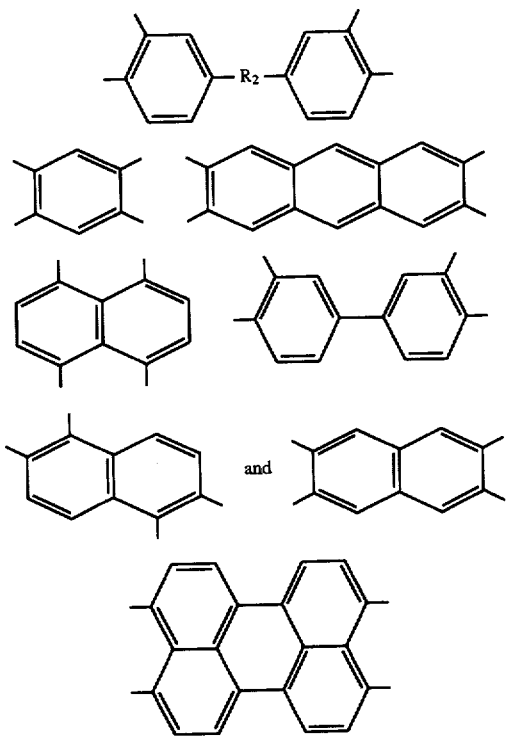

$R_2$ being selected from the group consisting of divalent aliphatic hydrocarbon radicals, having from 1 to 4 carbon atoms and carbonyl, oxy, sulfo, sulfide, ether, siloxane, phosphine oxide, hexafluoroisopropylidene and sulfonyl radicals and in which $R_1$ is at least one divalent radical selected from the group consisting of an aliphatic organic radical or from the group shown:

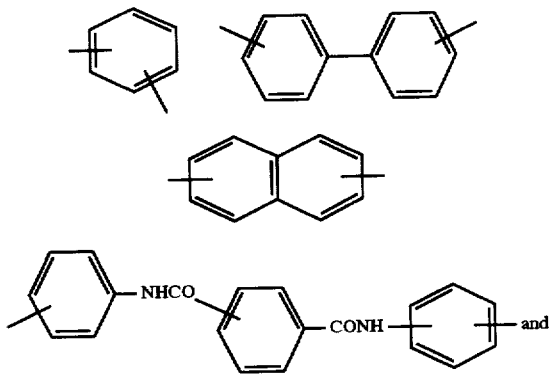

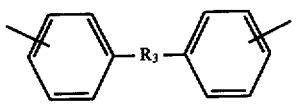

in which $R_3$ is a divalent organic radical selected from the group consisting of $R_2$,silico, and amino radicals. Polymers containing two or more of the R and/or $R_1$ radicals, especially multiple series of $R_1$ containing amido radicals, can be used.

Polyimides are available commercially from a variety of suppliers in one of four forms: a) as solutions of the polyamic acid precursors (e.g., DuPont Pyralin®; b) as pre-imidized polyimide film (e.g., DuPont Kapton® film); c) as pre-imidized powders (e.g., Ciba-Geigy Matrimid 5218® or solutions (e.g., Ciba-Geigy Probimide); or d) as solutions of the polyamic ester precursors (e.g., Ciba-Geigy mPaete). The chemistry of commercial polyimides includes examples of many of the components listed above, but a preferred polymer for use pursuant to the present invention is mPaete, which is based on the monomers pyromellitic dianhydride (PMDA) and oxydianiline (ODA, also named 4,4'-diaminodiphenyl ether). Other preferred polymers for use pursuant to the present invention are the polymers of benzophenonetetracarboxylic dianhydride (BTDA) and ODA and/or 1,3-phenylenediamine and the polymer of 3,3'-biphenylenetaracarboxylic acid (BPDA) and 1,4-phenylenediamine (PDA). Polyimide films based on PMDA-ODA are also available from Allied Corporation under the trade name Apical® and from Du Pont under the trade name Kapton®. Films based on BPDA-PDA are available from Ube Corporation as Upilex® and from Hitachi Chemical Company as PIQ-L100. Other trade name polyimides useful pursuant to the present invention include Durimid® from Rogers Corporation and the Du Pont Pyralin® series, including PI-2525 and PI-2566.

The substrate is selectively metallized to provide a pattern of copper or molybdenum lines thereon by usual processing to provide such. For instance, copper can be deposited from an electroless plating bath. Prior to plating, those portions of the substrate upon which the copper is to be plated are treated to render such susceptible to being plated from an electroless bath. Suitable processes are disclosed in U.S. Pat. Nos. 5,135,779 and 5,242,713 to Viehbeck et al. and assigned to International Business Machines Corporation, the assignee of the present application, disclosures of which are incorporated herein by reference. Also see Viehbeck et al., Redox Seeding and Electroless Metallization of Polyimides, Chapter 29, pp. 394–414, ACS Symposium Series 440, Metallization of Polymers, Sacher et al., Editor, American Chemical Society, Washington, D.C. 1990.

In particular, the process comprises supplying electrons to redox sites (i.e., sites which can undergo reduction and oxidation) of the polymeric material with concurrent uptake of counter cations from the electrolyte. The reduced polymeric material is then placed into contact with a solution that contains cations of a metal which will diffuse into the organic polymeric material and contact the redox sites thereof.

Metal deposited in such a manner can mediate continued electron transfer from the polymer resulting in further metal deposition near the previously deposited metal. The redox sites thereby transfer electrons to the cation that is energetically disposed to receiving electrons from the redox sites to thereby reduce the cation to metal atoms in the zero oxidation state. Next, a second metal is deposited from an electroless plating bath onto the zero oxidation metal.

The electrons are supplied to the redox sites of the polymeric material by either means of a cathode in an electrochemical circuit, the potential applied to the cathode being equal to or negative of the reduction potential of the polymer or preferably by means of a reducing agent in solution, the oxidation potential of the reducing agent being negative with respect to the reduction potential of the polymer. Alternatively, the electrons can be supplied to the redox sites of the polymeric material by contacting the polymeric material with tetrakis(dimethylamino)ethylene. The reducing agent may be in a charged or neutral form.

The reduction can be achieved by means of a reducing agent that has an oxidation potential negative with respect to the reduction potential of the polymer. Compounds such as berzil anion, anthraquinone anion, benzophenone anion, benzoin dianion, sodium naphtlhalenide, anion of N,N'-di-n-butylpyromellitimide and even solvated electrons generated, for example, in liquid ammonia can be used as the reducing agent.

The reducing agents can be reducing agents, per se, or produced such as in situ by electrochemical means. The reducing agents can be generated by chemical reaction such as by reacting benzoin and potassium tert-butoxide or be a compound having a strong electron donating power such as tetrakis(dimethylamino)ethylene.

Examples of suitable organic compounds that can be electrochemically reduced to provide the chemical reducing agent include, but are not limited to, the following groups of compounds: unsaturated aromatic hydrocarbons (e.g., anthracene), aldehydes and ketones (e.g., benzadehyde dibenzoylmethane), imides (e.g., N-n-butylphthalimide, N,N'-di-n-butyl-3,3',4,4'-biphenyl tetracarboxylic diimide), carbodiimides (e.g., bis-(p-chlorphenyl carbodiimide), aromatic heterocyclic nitrogen compounds (e.g., 9,10-diazaphenathrene), anhydrides (e.g., 1,8-napthalic anhydride, 3,3',4,4'-benzophenone tetracarboxylic dianhydride), quinones (e.g., 9,10-anthraquinone), quaternary aromatic nitrogen compounds (e.g., 1-ethylpyridinium bromide), azomethines (e.g., N-p-biphenylbenzalimine), immonium salts (e.g., N-ethyl-N-methyl benzophenone immonium salt), azo compounds (e.g., 4,4'-azobiphenyl), amine oxides (e.g., acridine N-oxide), nitro and nitroso compounds (e.g., 2-t-butylnitrobenzene), and organometallic compounds (e.g., diphenylchromium (I) iodide).

Benzil 9-fluorenone, benzophenone and anthracene are examples of specific compounds that can be reduced to provide the chemical reducing agents suitable for carrying out the present invention. The compounds can be reduced by applying such to an electrochemical cell containing an anode and a cathode and then applying a voltage.

The compounds can be reduced electrochemically or by bulk electrolysis. Typically, this is done using a two-compartment cell whereby the compartments are separated by a sintered glass disk or frit having a porosit, of less than 8 µm. A salt bridge or semi-permeable membrane also could be used to separate the compartments. The working compartment is housed with a cathode electrode which is comprised of a metal such as platinum, mercury, or stainless steel. The anode electrode is comprised of a conductor such as platinum, carbon, or stainless steel. For potentiostatic operation, an appropriate reference electrode is positioned in the working compartment (e g. Ag/0.1M AgNO$_3$). The cell can be purged with an inert gas such as N$_2$ or argon using an inlet tube and one-way valve or operation can be done in a glove box under an inert atmosphere.

Electrochemical generation of the reducing agent is accomplished by either galvanostatic, potentiostatic, or voltage-controlled electrolysis. Typically, the current density range for galvanostatic reduction is 0.1 to 2 mA/cm$^2$. In potentiostatic mode, reduction is typically done by applying a potential to the cathode which is more negative (e.g., -50 mV or more) than the reduction potential for the organic compounds as measured against the same reference electrode.

Compounds such as potassium tert-butoxide can react with aromatic ketones and alcohols to form anionic species. For instance, potassium tert-butoxide reacts with benzoin to form the benzoin dianion.

In addition, the composition used to reduce the polymer will include in the solution as supporting electrolyte and preferably a supporting electrolyte salt that contains as cation a member from one or the following groups: tetraalkylammonium, tetraalkylphosphonium, alkali metal, aryl-alkylammonium, aryl-alkylphosphonium, or chelated metal. The preferred tetraalkylammonium group is tetrabutylammonium, but other tetraalkyls with alkyl group being methyl, ethyl, propyl, isopropyl, pentyl, hexyl or mixed alkyl thereof can be employed if desired. An example of a typical aryl group is phenyl and an aryl-alkylammonium is benzyl-tributylammonium. An example of a chelated metal cation is potassium 18-crown-6. The supporting electrolyte salt preferably contains an anion one of the following: tetralfuoroborate, hexafluorophosphate, aryl sulfonate, perchlorate, or halide such as bromide or iodide.

The electrolyte solution is preferably comprised of an aprotic solvent. The aprotic solvents suitable for use in this invention include, but are not limited to, the following: nitrile and nitro compounds (e.g., acetonitrile, benzonitrile, nitromethane, amide and cyclic amide compounds (e.g., N,N-dimethylformamide, N-methylformamide, N,N-diethylformamide, N-ethylformamide, N,N-dimethylacetamide, N-methyl-2-pyrrolidone, hexamethylphosphoramide, ester, cyclic ester, and ether compounds (e.g., propylene carbonate, ethylene carbonate, γ-butyrolactone, ethyl acetate, tetrahydrofuran, dimethylether), oxide and sulfo compounds (e.g., dimethylsulfoxide, acetone, liquid sulfur dioxide, sulfolane, dimethylsulfone).

The reducing agents generated electrochemically, are typically neutral organic molecules which are electrochemically charged, thereby transferring electrons to the polymer, thereby reducing it. The electron transfer returns the reducing agent back to its neutral state.

The electrons can be supplied by contacting the polymeric material with tetrakis(dimethylamino)ethylene (TKDE).

The TKDE can be used as such or employed in solution with an organic solvent including the aprotic solvents discussed above. Also, protic solvents such as water and alcohols including methanol, ethanol, and ethylene glycol can be used provided such are made alkaline (e.g., adding a base).

The polyimide, which, after being reduced by the agent contains portions of reduced polyimide near the exposed surface can then be exposed to a solution of the metal ion in order to provide the metallic sites or seeds for subsequent metallic plating.

In particular, the solution can contain a cation of the desired metal such as palladium, platinum, silver, gold, copper, cobalt, and nickel which will contact the redox sites of the polyimide. The redox sites, which are in the, reduced state, will thereby transfer electrons to the In addition, an alternative process can be used for depositing the seed metal. In this case, the polymer film is contacted with a solution of the metal cations in a solvent which will cause swelling of the polymer film and concurrent absorption of metal cations. Exposure of the swollen film to a solution of the reducing agent can then cause reduction of the seed metal cations to the metallic state. It is preferable to wash any salt from the surface of the polyimide film prior to contact with the solution of the reducing agent. The depth or positioning of the metal deposition will then depend on the relative rate of diffusion of the electrons from the reducing agent into the film versus that of the cations out of the film. These rates are controllable by adjusting the concentrations of the reactant and, therefore, the position of the metal ions beneath the surface for good adhesion can be readily controlled.

The electrons can be supplied to the redox sites of the polymeric material also by employing electrochemical means. In particular, the process involved requires providing the polymer onto a metal electrode which, when negatively biased, acts as a cathode in the circuit.

A typical arrangement to carry out this particular procedure pursuant to the present invention is illustrated in U.S. Pat. No. 4,512,855.

The combination of the electrode and polymeric film is then immersed into an electrolyte solution in an aprotic solvent.

In addition, the composition used to reduce the polymer will include in the solution a supporting electrolyte and preferably a supporting electrolyte salt that contains as cation a member from one of the following groups: tetraalkylammonium, tetraalkylphosphonium, alkali metal, aryl-alkylammonium, aryl-alkylphosphonium, or chelated metal. The preferred tetraalkylammonium group is tetrabutylammonium, but other tetraalkyls with alkyd group being methyl, ethyl propyl, isopropyl, pentryl, hexyl, or mixed alkyl thereof can be employed if desired. An example of a typical aryl group is phenyl and an aryl-alkylammonium is benzyltributylammonium. An example of a chelated metal cation is potassium 18-crown-6. The supporting electrolyte salt preferably contains as anion one of the following tetrafluoroborate, hexafluorophosphorate, aryl sulfonate, perchlorate, or halide such as bromide or iodide.

The electrolyte solution is preferably an aprotic solvent. The aprotic solvents suitable for use in this invention include, but are not limited to, the following: nitrite and nitro compounds (e.g., acetonitrile, benzonitrdie, nitromethane), amide and cyclic amide compounds (N,N-dimethylformamide, N-methylformamide, N,N-diethylformamide, N-ethylformamide, N,N-dimethylacetamide, N-methyl-2-pyrrolidone, hexamethylphosphoramide, ester, cyclic ester), and ether compounds (e.g., propylene carbonate, ethylene carbonate, γ-butyrolactone, ethyl acetate, tetrahydrofuran, dimethylether), oxide and sulfa compounds (e.g., dimethylsulfoxide, acetone, liquid sulfur dioxide, sulfolane, dimethylsulfone).

The metal cations can be deposited both by being present in the solution of the electrolyte or introduced after the film has been reduced. The concentration of the supporting electrolyte in solution is usually about 1 to 0.01M, preferably about 0.2 to about 0.05M. Also, the concentration of the metallic cations in order to control the depth of the diffusion to not more than 1,000 angstroms is usually less than about 0.010M and generally from about 0.005 to about 0.0001M.

Since metal will deposit only at the surface regions of the reduced polymer, selective surface activation is readily obtainable by employing a resist mask or permanent resist on the polymeric film.

Materials which can be used as a mask include metals and photoresists such as Waycoat SC (J. P. Hunt) or KTFR (Kodak).

The reduced polymer sites act as the catalyst whereby the electroless metal plating is initiated by electron transfer from reduced polymer sites to metal cations in the electroless bath which deposits metal in situ and permits continued electroless plating due to the oxidation of the reducing agent provided in the electroless plating bath.

After the polymer is conditioned to render it susceptible for subsequent deposition of a metal from an electroless metal plating bath, the film is exposed to an electroless metal plating bath. Suitable metals include copper, nickel, gold, palladium, cobalt, silver, platinum, tin, or mixtures thereof. The preferred metals are copper, nickel, and palladium. Suitable copper electroless plating baths and their method of application are disclosed in U.S. Pat. Nos. 3,844,799 and 4,152,467, disclosures of which are incorporated herein by reference, except that it is preferred to use a low cyanide concentration or exclude the cyanide for purposes of this invention.

The copper electroless plating bath is generally an aqueous composition that includes a source of cupric ion, a reducing agent, a complexing agent for the cupric ion, and a pH adjuster. Such also usually includes a cyanide ion source and a surface-active agent. Cyanide ions should be excluded or controlled to low levels (i.e., 1–4 ppm) when using a surface seeded with Pd metal in accordance with the presence intention since the cyanide can complex and dissolve the Pd.

The cupric ion source generally used is cupric sulfate or a cupric salt to the complexing agent to be employed.

When employing cupric sulfate, it is usually employed in amounts of about 3 to about 15 grams/liter and more usually from about 8 to about 12 grams/liter. The most common reducing agent is formaldehyde which is generally used in amounts from about 0.7 to about 7 grams/liter and more usually about 0.7 to about 2.2 grams liter.

Examples of some suitable complexing agents include Rochelle salts, ethylenediaminetetraacetic acid, the sodium (mono-, di-, tri-, and tetra-sodium) salts of ethylenediaminetetraacetic acid, nitrolotetraacetic acid and its alkali salts, gluonic acid, gluconates, triethanolamine, glucono-(gamma)-lactone, and modified ethylenediamine acetates such as N-hydroethylethylenediaminetriacetate. In addition, a number of other suitable cupric complexing agents are suggested in U.S. Pat. Nos. 2,996,407; 3,075,856; 3,075,855; and 2,938,805. The amount of complexing agents dependent upon the amount of cupric ions present in solution is generally from about 20 to about 50 grams/liter or in a 3–4 fold molar excess.

The plating bath also usually contains a surfactant that assists in wetting the surface to be coated. A satisfactory surfactant is, for instance, an organic phosphate ester available under the trade designation GAFAC RE-610. Generally, the surfactant is present in amounts from about 0.02 to about 0.03 grams/liter. Also, the pH of the bath is generally controlled, for instance, by the addition of a basic compound such as sodium hydroxide or potassium hydroxide in the desired amount to achieve the desired pH. The pH is usually between about 11.6 and 11.8.

The plating baths generally have a specific gravity within the range of 1.060 to 1.080. The temperature of he bath is usually maintained between 70° C. and 80° C., and more usually between 70° C. and 75° C. The $O_2$ content of the bath is generally contained between about 2 ppm and about 4 ppm and more usually about 2.5 ppm to about 3.5 ppm by injecting oxygen and an inert gas into the bath. The overall flow rate into the bath is usually from about 1 to about 20 SCFM per thousand gallons of bath.

The metallized substrate is next coated with an inspection layer pursuant to the present invention. The inspection layer can be a light reflecting metal. The effectiveness of the inspection layer can be enhanced by introducing a light absorbing organic compound at certain regions of the inspection layer. In the case of a light reflecting metal, the inspection layer is selectively coated onto all of the copper or molybdenum features (i.e., the top or exposed copper or molybdenum), but not the non-metallized portions of the substrate. Typically, the thickness of the light reflecting metal is about 1 nm to about 200 nm, and more typically, about 10 nm to about 50 nm. In the case, of a light absorbing organic compound, such is provided either on buried copper or molybdenum lines or preferably on the non-metallized portions of the substrate.

The light reflecting metal deposited onto the exposed copper or molybdenum features should ideally have a reflection coefficient for incandescent light greater than the value for copper of 0.63 or for molybdenum. Examples of suitable metals include cobalt, gold (0.75), nickel (0.64), and silver (0.93). Other metals such as Pd and Pt have higher reflectivities at specific wavelengths used in automated optical testing are suitable, as well as alloys and/or mixtures of the above disclosed metals with each other or with minor amounts (up to a maximum of about 20 wt. %) of other materials. Palladium is the preferred metal because of ease of application. For instance, when cobalt is deposited, it is typically deposited from an electroless bath which can result in the presence of such materials as P and/or B. The reflecting metal can be coated using any known composition for such purposes. For example, the Pd can be coated onto the copper lines from an aqueous solution of palladium sulfate and sulfuric acid.

Examples of suitable light absorbing organic compounds are dyes having aromatic moieties.

The treated substrate is then optically imaged in order to inspect it for defects in the copper or molybdenum lines such as opens and shorts therein. Any of the currently available tools and techniques can be used for this purpose. One such tool being Orbot WF-720 Water Inspection System from Orbot Instruments Inc. The imaging with the Orbot WF-720 involves scanning using normal illumination of a focused 488 nm argon laser beam. The defects will be seen as bright specs against a dark background.

After the imaging, the inspection layer is removed such as by dissolving it in a solvent or by a plasma etch. The removal process should not adversely effect the copper lines or molybdenum lines, the substrate or the copper-substrate bond or molybdenum-substrate bond. The metallic inspection layer can be removed by dissolving in an inorganic acid such as dilute sulfuric acid, phosphoric acid, nitric acid or hydrochloric acid, typically at concentrations of 0.1M to 5.0M. Plasma (or RIE) using $O_2$,Ar, $CF_4$ or $N_2$ gases can remove the light-absorbing organic compounds.

Prior to the removal with acid, the substrate can be contacted with a base such as 5–10% sodium hydroxide, $NH_4OH$, $N(CH_3)_4$ OH, and KOH to enhance adhesion between polyimide layers to each other. After the base and after the acid treatment, the substrate can be rinsed in deionized water.

The present invention is especially advantageous for fabricating multilevel thin film packages. In such instances, the article can be contacted with an adhesion promoter to enhance adhesion between the copper lines and subsequently to be applied polymeric substrate, such as the polyimide for constructing the next level. A particular adhesion promoter is a N-methyl-pyrrolidone (NMP)-based promoter such as disclosed in Lee et al., Low-Cost and High-Temperature Stable Adhesion Promoter for Polymer-to-Copper Interface: Organic Compounds Containing Triazole or Imidazole Functionality. IBM Technical Disclosure Bulletin. Volume 37, No. 5. p. 221, May 1994, disclosure of which is incorporated herein by reference. This procedure employs a monomeric compound that contains triazole or imidazole functional group. For high thermal stability, triazole (or imidazole) with heterocyclic unit(s) is employed. Typical compounds are 8-azaadenine, adenine, 5-aminobenzotriazole, benzotriazole-5-carboxylic acid aminobenzimidazole, 6-n-octylmercaptopurine, and other compounds containing triazole and imidazole functional groups. 8-Azaadenine and adenine provide a good adhesion for the polyimide/Cu interface. Peel straights are about 35–50 g/mm. This treatment also prevents corrosion of the copper.

Another type of adhesion promoter is triazole- or imidazole-containing polymer such as poly(arylene ether benzimidazole). Suitable materials are disclosed in U.S. Pat. Nos. 5,516,874 and 5,582,858 to Lee et al, and assigned to International Business Machines Corporation, the assignee of the present application. Also, see Lee et al. Journal of Adhesion Science and Technology, Volume 9, pp. 1125–1141 (1995) as well as Volume 10, pp. 807–821 (1996). The polymer adhesion promoter also acts as a diffusion barrier between polyamic acid and copper substrates as disclosed by Lee et al, in the above references. A-1100 and AP420™ are known to be good adhesion promoters. A-1100 which is 3-aminopropyltriethoxysilane is diluted in water prior to use. AP420™ is from Toray and its solvent is known to be an alcohol such as 2-propanol.

Next, a polyimide layer can be provided for fabricating the next level and the above process repeated along with conventional processing steps to the extent to obtain the desired number of levels.

The following non-limiting examples are presented to illustrate the present invention.

A thin layer of Pd (20 nm) was plated onto copper on a 2.25"-Si wafer from a palladium sulfate and sulfuric acid solution. The Pd layer was easily detected by the Orbot inspection tool. This Pd layer was removed using a dilute sulfuric acid (1.0M), which can be employed in the wet process for polyimide-to-polyimide adhesion.

After the Pd layer was removed, a 8-azadenine solution (0.3%) in NMP as adhesion promoter was spin-coated onto the (exposed) Cu substrate followed by spin-coating and curing mPaete. A 90 ° peel strength was measured with a MTS tool. The peel strengths were 35–50 g/mm which is acceptable for the application.

Using adenine as an adhesion promoter gave a similar result. When using A-1100 and AP420 in an alcohol/water solvent as adhesion promoter, the device should be baked after spin-coating.

What is claimed is:

1. Method for inspecting copper lines or molybdenum lines on a substrate for defects in said lines which comprises selectively metallizing a substrate with copper lines or molybdenum lines;

selectively coating the substrate having said copper lines or molybdenum lines with an inspection layer wherein said inspection layer is located on said copper lines or said molybdenum lines, or on said substrate, then imaging the substrate;

and removing said inspection layer after the imaging.

2. The method of claim 1 wherein said inspection layer comprises light reflecting metal coated onto the copper or molybdenum.

3. The method of claim 2 wherein said reflecting metal is selected from the group consisting of Pd, Pt, Ni, Au, Ag, Co, alloys thereof, and mixtures thereof.

4. The method of claim 3 which further includes a light-absorbing organic compound located on copper lines buried beneath said substrate.

5. The method of claim 3 which further includes a light-absorbing organic compound located on said substrate.

6. The method of claim 5 wherein said compound contains aromatic moiety.

7. The method of claim 2 wherein said metal is Pd.

8. The method of claim 1 wherein said inspection layer is removed by wet processing.

9. The method of claim 8 wherein said wet processing comprises treating in an inorganic acid selected from the group consisting of sulfuric acid, phosphoric acid, nitric acid and hydrochloric acid.

10. The method of claim 1 wherein said substrate is a polyimide.

11. Method for inspecting copper lines or molybdenum lines on a substrate for defects in said lines and for fabricating a multilevel thin film package which comprises
   a) selectively metallizing a first substrate with copper lines or molybdenum lines;
   b) selectively coating the substrate having said copper lines or molybdenum lines with an inspection layer wherein said inspection layer is located on said copper lines or molybdenum lines on said substrate, then imaging the substrate;
   c) removing said inspection layer after the imaging: and
   d) then providing a second layer of a selectively metallized second substrate over the first substrate and repeating steps b to d to provide the desired number of levels.

12. The method of claim 11 which further comprises in step c) treating said first substrate with a base and then an acid to enhance adhesion between the substrates and with an adhesion promoter to enhance adhesion between the copper lines and second substrate.

13. The process of claim 12 where said adhesion promoter contains triazole or imidazole functionalities.

14. The process of claim 12 wherein said adhesion promoter is triazole- or imidazole-containing polymer.

15. The method of claim 14 wherein said triazole- or imidazole-containing polymer is poly(arylene ether benzimidazole).

16. The process of claim 12 wherein said adhesion promoter is AP420™ or A-1100.

17. The method of claim 11 which further comprises between steps c) and d) treating said first substrate with plasma to enhance adhesion between substrates and with an adhesion promoter to enhance adhesion between the copper lines and second substrate.

18. The process of claim 17 where said adhesion promoter contains triazole or imidazole functionalities.

19. The process of claim 17 where said adhesion promoter is triazole-or imidazole-containing, polymer.

20. The method of claim 19 where said triazole- or imidazole-containing polymer is poly(arylene ether benzimidazole).

21. The process of claim 17 where said adhesion promoter is AP420™ or A-1100.

22. The method of claim 17 where said plasma includes reactive ion etching, down-stream ashing and direct plasma.

23. The method of claim 11 wherein said inspection layer comprises light reflecting metal coated onto the copper.

24. The method of claim 23 wherein said reflecting metal is selected from the group consisting of Pd, Pt, Ni, Au, Ag, Co, alloys thereof, and mixtures thereof.

25. The method of claim 23 wherein said metal is Pd.

26. The method of claim 23 which further includes a light-absorbing organic compound located on said substrate.

27. The method of claim 26 wherein said compound contains aromatic moiety.

28. The method of claim 23 which further includes a light-absorbing organic compound located on copper lines buried beneath said substrate.

29. The method of claim 11 wherein said inspection layer is removed by wet processing.

30. The method of claim 29 wherein said wet processing comprises treating in an inorganic acid selected from the group consisting of sulfuric acid, phosphoric acid, nitric acid and hydrochloric acid.

31. The method of claim 11 wherein said substrate is a polyimide.

* * * * *